United States Patent [19]

Fydelor et al.

[11] 4,377,010

[45] Mar. 22, 1983

[54] BIOCOMPATIBLE MATERIAL COMPRISING A BASE POLYMER BULK GRAFT POLYMERIZED WITH AN ETHYLENICALLY UNSATURATED CARBOXYLIC ACID

[75] Inventors: Peter J. Fydelor, Swindon; David E. M. Taylor, Hounslow, both of England

[73] Assignee: The Secretary of State for Defence in Her Britannic Majesty's Government of the United Kingdom of Great Britain and Northern Ireland, London, England

[21] Appl. No.: 90,084

[22] Filed: Oct. 31, 1979

[30] Foreign Application Priority Data

Nov. 8, 1978 [GB] United Kingdom ............... 43624/78

[51] Int. Cl.³ .......................... A61F 1/22; A61F 1/24
[52] U.S. Cl. ................................. 3/1.4; 3/1;
3/1.5; 128/92 C; 128/92 D; 128/113; 128/130;
128/156; 128/335.5; 210/500.1; 210/500.2;
424/DIG. 7; 428/413; 428/421; 428/422;
428/447; 428/451; 428/483; 428/507; 428/508;
428/515; 428/516; 428/520; 433/201;
428/424.2
[58] Field of Search .............................. 3/1, 1.4, 1.5;
128/92 C, 92 D, 113, 130, 156, 335.5, 348, 349;
210/500 M, 500 R; 424/DIG. 7; 428/421, 422,
413, 425, 447, 451, 483, 507, 508, 515, 516, 520;
433/201

[56] References Cited

U.S. PATENT DOCUMENTS

| 2,668,162 | 2/1954 | Lowe . |
| 2,676,945 | 4/1954 | Higgins . |
| 3,044,942 | 7/1962 | Baptist . |
| 3,886,947 | 6/1975 | Sawyer ................................. 3/1.4 |
| 3,943,045 | 3/1976 | Cordrey et al. ....................... 3/1 |
| 4,143,218 | 3/1979 | Adams et al. ...................... 427/444 |
| 4,178,329 | 12/1979 | Becker et al. ........................ 3/1.4 |

FOREIGN PATENT DOCUMENTS

| 2541527 | 3/1976 | Fed. Rep. of Germany . |
| 602131 | 5/1948 | United Kingdom . |
| 749739 | 5/1956 | United Kingdom . |
| 761840 | 11/1956 | United Kingdom . |
| 1043008 | 9/1966 | United Kingdom . |
| 1043518 | 9/1966 | United Kingdom . |
| 1141271 | 1/1969 | United Kingdom . |
| 1490128 | 10/1970 | United Kingdom . |
| 1236596 | 6/1971 | United Kingdom . |
| 1302619 | 1/1973 | United Kingdom . |
| 1451891 | 10/1976 | United Kingdom . |
| 1451892 | 10/1976 | United Kingdom . |
| 1504101 | 3/1978 | United Kingdom . |
| 1549352 | 8/1979 | United Kingdom . |

OTHER PUBLICATIONS

M. L. Miller et al., J. App. Polymes Sci., 1970, 14, 257.

*Primary Examiner*—James C. Cannon
*Attorney, Agent, or Firm*—Cushman, Darby & Cushman

[57] ABSTRACT

A biocompatible surgical device comprises at least at its surface a hydrophilic thermoplastic graft copolymer which is an ethylenic carboxylic acid, selected from acrylic acid and alkyl substituted acrylic acids graft copolymerized onto a base polymer. The base polymer is preferably selected from polyolefins, especially polyethylene and polypropylene, partially and fully fluorinated polyolefins, especially polytetrafluoroethylene and polyetherurethanes.

Graft copolymerization of the monomers to the base polymer is initiated preferably by ionizing radiations, especially gamma radiation. The reaction takes place preferably in an aqueous solution and in the presence of a homopolymerization inhibitor such as ferrous sulphate or potassium ferricyanide.

The base polymer may be graft copolymerized throughout its entire thickness or to a known depth in one or more of its surfaces. The former material exhibits high elastic properties while the latter exhibits a low elasticity and low moduli.

The biocompatible devices described may be in the form of prostheses, especially vascular prostheses, wound dressings, especially in the treatment of skin loss and open wounds, and body fluid contacting surfaces for use in extra-corporeal, body fluid treating devices.

15 Claims, No Drawings

BIOCOMPATIBLE MATERIAL COMPRISING A BASE POLYMER BULK GRAFT POLYMERIZED WITH AN ETHYLENICALLY UNSATURATED CARBOXYLIC ACID

The present invention is concerned with the medical and veterinary use of synthetic plastics materials for implantation into or onto living mammalian bodies.

It is known to implant materials etc into or onto the living mammalian body in order to rectify or repair a malfunction or to replace in certain instances faulty or diseased parts. For example, heart valves may be replaced, as may be hip joints, and other examples are well known to those skilled in the art. However, as is also well known foreign bodies or materials in the mammalian body tend to excite hostile reaction and great care is necessary to select materials that are biocompatible. That is to say, to select materials that do not cause adverse biological response to the implant. For example, excessive blood clotting or scarring at the site of implantation. Relatively few materials meet this criterion, for example, stainless steel, titanium, titanium alloy, cobalt chrome alloy, pyrolytic carbon, vitreous carbon, polytetrafluoroethylene, polyethylene terephthalate and silicone rubber are those most commonly employed.

With the exception of devices manufactured from certain biodegradable materials, most devices in common use, that are brought into contact with mammalian blood, rely on the materials of which they are composed having either a totally inactive (non-thrombogenic) surface, extreme surface flatness or a negatively charged (cationic) surface. Current devices are constructed to be either homogeneous and ostensibly non-porous, or purposely microporous, comprising homogeneous material containing (with the exception of the carbons, vitreous and/or pyrolytic) continuous pores with dimension generally of the order 0.02 to 2.0 micrometers, or purposely macroporous, constructed by weaving or knitting continuous homogeneous filament, yarns which are, in some cases, uncut, and in others, cut, looped or napped to form a velour fabric.

Such biocompatible devices may be used to contain body fluids in extra-corporeal devices, such as heart-lung machines and kidney machines, and in the present specification the term biocompatible device is to be construed as including devices having such extra-corporeal uses as well as devices which can be directly applied to the outer surface of the body, as for example in the treatment of wounds and burns and devices which can be implanted into the living mammalian body.

In accordance with the present invention there is provided a biocompatible surgical device wherein at least the outer surface of each device comprises a hydrophilic thermoplastic graft copolymer which is an ethylenic carboxylic acid graft-copolymerised onto a base polymer. The preferred ethylenic carboxylic acid comprises acrylic acid or an alkyl substituted acrylic acid, especially methacrylic acid. The base polymer comprises one or more polymers selected from polyolefins, partially or fully fluorinated polyolefins, polyetherurethanes, polydimethyl siloxanes, polyethylene glycolterephthalates, polyamides, polyacrylonitriles, cellulosic based polymers, polyvinylchlorides, polyvinylidenechlorides, polyvinylalcohols, polyethyleneglycols polyvinylpyrrolidones mixtures of these polymers and copolymers of the monomers of said polymers. Preferably the base polymer is selected from homo- and co-polymers of olefins and partially and fully fluorinated olefins especially polyethylene, polypropylene and polytetrafluoroethylene. In a further preferred embodiment of this invention the base polymer is a polyetherurethane.

The co-polymer materials in the biocompatible devices in accordance with the present invention are produced by graft-copolymerisation, for example, as disclosed in UK Pat. Nos. 1,451,891 and 1,451,892, and the base polymer is generally pre-formed to the desired shape before the graft-copolymerisation reaction is carried out, although it is possible for the device to be formed after copolymerisation.

These devices may be used in any application which requires a biocompatible device because of the need to avoid adverse reactions in contact with the living mammalian body or body fluids. The copolymer material may comprise all of the device or merely the surface which will be in contact with the body fluids. In particular, these materials may be used as vascular prostheses in the veinous or arterial system, as heart patches or as heart valves, as a replacement for the brain membrane, as the outer encapsulant of implantable devices such as heart pacemakers, and as catheters or the outer sheath of catheters in contact with body fluids and the like. They may also be used as temporary coverings for skin loss resulting from either mechanical damage or burns, or they may be used as a covering for open wounds. Additionally these devices may be used as extra-corporeal devices to provide biocompatible channels through which body fluids may be passed in heart-lung and kidney machines, for example. Indeed the materials of these devices generally have the properties of semipermeable membranes and may be used as such in extra-corporeal devices.

The preformed polymer may be either non-porous, microporous or macroporous and may be in the form of a woven, knitted or textured structure. Whilst in the preferred embodiment of this invention the preformed polymer is uniformly graft-copolymerised throughout its entire thickness (bulk graft-copolymerised), the preformed polymer may be only partly graft-copolymerised to a known depth from its surface (surface graft-copolymerised) on any one or more of its surfaces. Therefore, where a device exhibiting high elastic properties is required then a bulk graft-copolymeric material will be preferred, whereas where the need is for a device with high moduli and low elasticity then a surface graft-copolymeric material will be chosen.

The graft-copolymerisation reaction is preferably carried out in a suitable solvent for the co-monomer although particularly where it is only necessary to carry out a graft-copolymerisation of the surface of the preformed polymer the co-monomer may be in the form of an undiluted liquid or a diluted or undiluted vapour or gas. The preferred solvent for the co-monomer is water, although other suitable solvents in which the said monomers can be dissolved include acetone, methanol, ethanol, butanol, benzene, xylene, toluene and hexane and mixtures of these solvents in any relative concentrations. Preferably the percentage of co-monomer in the graft-copolymerisation reaction mixture is in the range of 2% to 50% (volume/volume). Chain transfer agents, chain termination agents, free radical scavengers, surface scavengers and/or homopolymerisation inhibiting agents may be admixed with solvent containing co-monomer or with the co-monomer containing vapour or gas, as is commonly practiced in the graft-copolymerisation art.

In a preferred embodiment of the graft-copolymerisation reaction mixture the co-monomer is dissolved in water containing between 1 gm mol and 20 gm mol per liter of solution of a suitable homopolymerisation inhibitor selected from cupric chloride, cupric nitrate, certain organic inhibitors and most preferably, ferrous sulphate or potassium ferricyanide.

Initiation of the graft-copolymerisation of the monomers to the preformed polymer materials is preferably by ionising radiations but may also be by ultra-violet radiation, visible light, active species in an electrically sustained gas plasma, heat and chemical initiators such as organic peroxides and other free radical initiators or ionic initiators such as Lewis acids. Generally non-chemical is favoured over chemical initiation because of the problems associated with impregnation of the final device with a chemical initiator. Where initiation is by ionising radiations such as gamma photons or accelerated electrons the absorbed dose is preferably between $1 \times 10^5$ and $1.5 \times 10^6$ rad based upon a G ferric ion for the Fricke Dosimeter of 15.6.

Whereas bulk graft-copolymerisation is initiated by ionising radiations only, surface graft-copolymerisation may be initiated by any of methods previously described although ionising radiation, ultraviolet radiation and/or visible light are preferred. The percentage graft-copolymerisation (wt of acrylic acid in total weight of product actually copolymerised ie in surface graft-copolymerisation only the weight of the copolymerised regions is counted) is preferably between 5% and 45% for both bulk and surface graft-copolymerised devices.

Following graft-copolymerisation the product material is separated from the rest of the reaction mixture, ie solvents, residual monomer, homopolymer, residual scavengers or other additives, by any suitable means well known to those practised in the art. The final graft-copolymerised material may be left in its acid form or may alternatively be converted to and used in the form of a polymetallated salt preferably a polysodium, polypotassium or polycalcium salt. Further, it may also be conditioned by any number of chemical and/or thermal treatments, for example, those disclosed in U.S. Pat. No. 4,143,218, in which a film of hydrophilic polymeric material is immersed at an elevated temperature, for example in excess of 80° C., preferably above the crystalline melting point of the hydrophilic polymeric material. After this immersion, the liquid treatment medium is removed by quenching and washing in cold water or dilute alkaline solution. The liquid treatment medium is a hydroxyl containing organic liquid and suitable liquids include alkanols, for example octanol or decanol, polyhydric alcohols, for example, glycerol, mono-, di- or tri-ethylene glycol and polyethylene glycol and, although the liquid treatment medium is substantially non-aqueous, may also include azeotropic mixtures of alkanols and polyhydric alcohols containing less than about 20% by weight of water. The preferred liquid treatment medium is glycerol.

If the biocompatible device is to be formed or moulded into shape after graft-copolymerisation it can now be shaped as required by any conventional means.

Prior to its use the graft-copolymerised biocompatible device may be cleaned and sterilised by any well known means and may be conditioned in any extracellular or natural body fluids as deemed necessary by the medical practitioner or surgeon.

The present invention will now be described by way of example only by the description of synthesis of material for use in biocompatible devices in accordance with the present invention and by the description of in vivo tests in rats and dogs which illustrate the low reaction to the biocompatible material of these devices by the living mammalian body.

EXAMPLE 1

Preparation of material based upon high density polyethylene (hereinafter HDPE).

A film a HDPE 40 microns thick (supplied by the Metal Box Company Ltd under the trade name "Densothene") was rolled up with a single ply of absorbent interleaving material and placed in a vertical aluminium alloy reaction vessel which was then filled to a level above that of the roll of film with an aqueous solution containing 25% by volume of commercial grade stabilised acrylic acid (hereinafter AA), and 4 g of analytical grade ferrous sulphate per liter of monomer solution. The reaction vessel and contents were evacuated by a liquid ring pump for 20 minutes at the end of which time it was back filled with nominally oxygen-free nitrogen to a pressure just in excess of atmospheric pressure and then sealed. The reaction vessel and contents were irradiated with gamma rays from a 60 Co source at 20° C. to a total absorbed dose of $7.3 \times 10^5$ rad at a dose rate of $1.48 \times 10^5$ rad per hour. The graft-copolymerised film was removed from the reaction vessel then automatically washed first in tap water at 20° C., then in an N/10 hydrochloric acid solution at 20° C., then distilled water at 20° C. and finally dried in a warm air cabinet before being re-rolled onto a paper spool. The weight of graft-copolymerised acrylic acid was found to be 27.3% by weight based on the final copolymer weight and so far as could be determined was an homogeneous graft, the final "dry" thickness of the copolymer film was 50 microns and the equilibrium water content at ambient temperature found to be 19% by weight with some attendant swelling in film breadth and length compared to the original preformed polyethylene film.

The graft copolymerisations in the following examples were carried out in the same manner as Example 1 except for the changes indicated in the individual examples.

EXAMPLE 2

Low density polyethylene (hereinafter LDPE).

LDPE film of 38 microns thickness (supplied by the Metal Box Company Ltd under the trade name "Diothene") was copolymerised as described in Example 1 except that the total dose was 0.6 M rad at 24° C. at a dose rate of 0.0137 M rad/hour. The finally produced copolymer had a thickness of 32 microns and was grafted to the extent of 31.9% by weight of AA and also had a water uptake of 20% by weight.

EXAMPLE 3

Cast polypropylene film (hereinafter CPP).

A film of CPP of 32 microns thickness (supplied by Shorko Films Ltd) was copolymerised as described in Example 1 except that the total dose rate was 1.32 M rad at a dose rate of 0.0132 M rad/hour. The finally produced copolymer had a thickness of 38 microns and was grafted to the extent of 33.5% by weight of AA and also had a water uptake of 27% by weight.

EXAMPLE 4

Porous polypropylene (hereinafter PPP).

A film of PPP of thickness 25 microns (supplied by Celanese under the trade name of "Celgard") was graft copolymerised as described in Example 1 except that the grafting solution contained 30% by weight of acrylic acid and included 8 g/l of ferrous sulphate. The irradiation dose rate was 0.45 M rad/hour to a total dose of 1.0 M rad. The finally produced copolymer had a thickness of 28 microns and was grafted to the extent of 24.5% by weight of AA and also had a water uptake of 60% by weight.

EXAMPLE 5

Polytetrafluoroethylene (hereinafter PTFE)

A film of PTFE of thickness 25 microns (supplied by Polypenco Ltd) was graft copolymerised as described in Example 1 except that the grafting solution was a 12.5% by weight aqueous solution of AA containing 7 g/l of potassium ferricyanide. The irradiation dose rate was 0.0117 M rad/hour to a total dose of 0.75 M rad. The graft copolymer was heat treated in glycerol at 102° C. in its potassium salt form and had a final thickness of 25 microns. It was grafted to the extent of 19.4% by weight of AA and had a water uptake of 23% by weight.

EXAMPLE 6

Polyetherurethane (hereinafter Pu)

Pu film of 29 microns thickness of medical grade was copolymerised as described in Example 1 except that the aqueous solution contained 30% by volume of commercial grade stabilised acrylic acid (AA) and that the total dose was $9.3 \times 10^5$ rad at a dose rate of 0.0128 M rad/hour. The finally produced copolymer had a thickness of 32 microns and was grafted to the extent of 28.6% by weight of AA and also had a water uptake of 33% by weight.

EXAMPLE 7

Pu Heart Valve

A fully fabricated tricusp leaflet artificial heart valve of average thickness of flexible Pu portion 60 microns was copolymerised as in Example 1 except that the total dose was 0.67 Mr at a dose rate of 0.014 Mr/hour. The finally produced valve had a heterogeneous or surface graft on each of the two surfaces of the cusps and had a final graft weight of 4.2%. The graft copolymerisation was found to have had minimal effect upon the pulsatile mechanical properties of the valve and to have improved properties with regard to thrombus formation.

EXAMPLE 8

Polydimethylsiloxane (hereinafter PDMS)

PDMS porous silicone sheeting of 1000 microns thickness (supplied by Dow Corning as medical grade) was copolymerised as described in Example 1 except that the aqueous solution contained 30% by volume of commercial grade stabilised AA. The finally produced copolymer had a thickness of 1600 micron and was grafted to the extent of 35.2% by weight of AA and also had a water uptake of 159% by weight.

EXAMPLE 9

Nylon-12

A Nylon-12 film (supplied by Grilon Plastics) was copolymerised as in Example 1 except that the aqueous solution contained 75% by volume of commerical grade stabilised AA and that the total dose was 0.64 Mr at a dose rate of 0.0134 Mr/hour. The finally produced copolymer was grafted to the extent of 34.3% by weight of AA.

EXAMPLE 10

Nylon 6

A Nylon 6 film was copolymerised as in Example 1 except that the aqueous solution contained 5% by volume of commercial stabilised AA and that the total dose was 0.6 Mr at a dose rate of 0.03 Mr/hours. The finally produced copolymer was grafted to the extent of 22.5% by weight of AA.

EXAMPLE 11

Nylon 11

A Nylon 11 film was copolymerised as in Example 1 except that the aqueous solution contained 30% by volume of commercial stabilised AA and that the total dose was 0.7 Mr at a dose rate of 0.03 Mr/hour. The finally prepared copolymer was grafted to the extent of 37.4% by weight of AA.

These materials were tested for biocompatibility by implantation in rats and a control study was made by implanting a commercially available material, namely a knitted double velour polyester (marketed by Meadox Medicals Inc. under the name "Microvel").

The materials were cut into 1 cm² pieces and prepared for implantation by immersion in sterile compound sodium lactate (Hartmans Solution BP) for 48 hours. They were then ultrasonically cleaned by placing the glass containers in a sonic bath for 30 minutes and rinsed six times with sterile Hartman's Solution. The pieces were then placed between sterile swabs, packed and autoclaved so that they were in a hydrated state immediately prior to implantation.

The sites selected for implantation were as follows:
1. An incision was made in the sheath of the sacrospinalis at about the level of the fourth lumbar vertebra and the square of material inserted as deeply as possible into the muscle.
2. One piece was inserted into the peritoneal cavity.
3. A third piece was placed subcutaneously just lateral to the incision.

The rats were anaesthetised with Pentobarbitone Sodium (Sagatal) 600 mg/ml i.p. and the two small incisions closed with 2.5 Abralon braided silk. The stitches were not removed and only in three cases, which are noted below, was any adverse reaction observed. One rat died 3 hours after the implantation due to an overdose of anaesthetic and one died after 30 days but the cadaver was not retained for postmortem examination.

The biocompatibility tests were carried out on two groups of 20 rats each, four rats in each group receiving one of the materials under test.

The control group of rats numbered eight, weighing 150–200 gms and were six months old. The tests for biocompatibility were carried out on two groups of 20 rats each; the rats being 350 gms in weight and 18 months old.

The following Examples give the notes on post-mortem examination on sacrifice of the animals after 6 weeks and in interpreting these it should be noted that the materials of the devices of the present invention showed surprisingly and remarkably few signs of reaction by the host mammalian body to their presence. In general in the following, lack of mention of a piece of material implanted at a particular site indicates that in that particular animal at that particular site no adverse reaction was noted. It should also be noted that these materials are all at least translucent and in the absence of biological reaction, for example the formation of blood clots, can be very difficult to locate in the animal body.

EXAMPLE 12 first test group of rats.

(a) HDPE/AA (material prepared in accordance with Example 1)

Rat
1. Muscle implant had migrated into subcutaneous tissue and was slightly ingrown. No peritoneal implant found. Subcutaneous implant slightly adherent.
2. No adverse reactions apparent.
3. Subcutaneous tumour, equivalent to stitch reaction, at laparotomy incision. Peritoneal implant adherent under surface of diaphragm.
4. Muscle implant migrated into subcutaneous tissue. Subcutaneous implant very adherent.

(b) LDPE/AA (Material prepared in accordance with Example 2).

Rat
1. Subcutaneous implant not visible but may be in tissue removed for histological examination. Peritoneal implant migrated under right lobe of liver-predunoulated attachment.
2. Muscle implant migrated into subcutaneous tissue. Peritoneal implant adherent to loop of ileum with some fibrous reaction. Pale, slightly enlarged liver.
3. No evidence of peritoneal material.
4. No adverse reactions apparent.

(c) CPP/AA (Material prepared in accordance with Example 3).

Rat
1. No adverse reactions apparent.
2. Peritoneal implant adherent to both liver and diaphragm under left dome.
3. Peritoneal implant adherent to diaphragm.
4. Peritoneal implant free.

(d) PPP/AA (Material prepared in accordance with Example 4).

Rat
1. Muscle implant fell out, material completely dried out. Subcutaneous implant completely dried out.
2. Peritoneal implant free.
3. Animal died three hours after implant due to an overdose of anaesthetic.
4. Animal died 30 days after implant, cause unknown as no postmortem examination was carried out.

(e) PTFE/AA (Material prepared in accordance with Example 5).

Rat

| | |
|---|---|
| 1 2 3 | No peritoneal implant was found. There was no macroscopic evidence of the material, no adhesion and no sign of peritonitis. |

4. Subcutaneous implant has migrated 1" laterally from implanted position. No adhesions found.

EXAMPLE 13

Second test group of 20 rats.

(a) HDPE/AA (Material prepared in accordance with Example 1).

Rat
1. Peritoneal implant adherent to greater omentum.
2. Subcutaneous implant dried out and non-adherent. Small switch reaction in belly. Peritoneal implant dried out and loose in cavity.
3. Peritoneal implant dried out and adherent to diaphragm under right lobe.
4. Muscle implant completely dried out and fell out when incision was made. Peritoneal implant adherent to greater omentum. Haemorrhagic appearance in implant. Area of stitch reaction around right abdomen, section taken for histological examination. Liver very friable.

(b) LDPE/AA (Material prepared in accordance with Example 2).

Rat
1. Muscle implant migrated into subcutaneous tissue. Peritoneal implant in greater omentum.
2. Peritoneal implant adherent to greater omentum,
3. Muscle implant not found. Peritoneal implant adherent to greater omentum.
4. Peritoneal implant adherent to ileum.

(c) CPP/AA (Material prepared in accordance with Example 3).

Rat
1. Muscle implant rather dry and lying loose. Subcutaneous implant lying free, no reaction. No peritoneal implant found.
2. Muscle implant migrated into subcutaneous tissue. Subcutaneous implant migrated and non-adherent. Peritoneal implant floating free in cavity.
3. Muscle implant migrated into subcutaneous tissue. Subcutaneous implant migrated and rolled into tight wad of material. Peritoneal implant not found.
4. All pieces found. All non-adherent.

NOTE: This material is almost transparent and is therefore difficult to locate in the peritoneal cavity.

(d) PPP/AA (Material prepared in accordance with Example 4).

Rat
1. Peritoneal implant adherent under diaphragm. Liver very friable.
2. No peritoneal implant found.
3. No muscle implant found and no subcutaneous implant found.
4. All pieces found.

(e) PTFE/AA (Material prepared in accordance with Example 5).

Rat
1 Peritoneal implant adherent to abdominal wall.
2 Query as to whether material is in section of muscle taken, no signs of it having migrated. Peritoneal implant adherent to caecum.
3 No peritoneal implant found.
4 Peritoneal implant adherent to greater omentum.

EXAMPLE 14

Control Group of 8 rats implanted with double velour polyester (Dacron Microvel-Meadox Corporation)

All pieces of implant material were adherent to tissue.

Subcutaneous

Implant dry and hard as might be expected in such a site. All pieces covered with thin layer of tissue growth. C6 had small cyst/abscess on one corner of implant material not due to stitch reaction. No sign of infection in surrounding tissue.

Peritoneal

Adherent in most cases to lesser omentum, covered by thin layer of tissue. No adverse reaction.

Muscle

Implant had migrated as could be expected from size if implant in ratio to size of muscle sheath. This site showed the highest proportion of fibrosis, but this was not excessive. Cl was missing due to stitches being removed by rat and implant must have been lost before re-suturing was done.

Liver

Healthy in all 8 animals.

Kidneys

All appeared healthy, C7 had small cyst/abscess about 1 cm distal from L kidney embedded in surrounding fatty tissue.

The histological differences between the tissue reaction to the test material as against the control material were:
(a) The fibrous capsule is much thinner e.g. on intra muscular implantation 40μ for material 4 as against 100μ for the Dacron Velour.
(b) The collagen is more tightly packed and more mature collagen is present in the capsules surrounding the test materials.
(c) There was minimal cellular infiltration apart from fibro blasts around the test materials, whereas at 3 months there was considerable infiltration around the control material of lymphocyes and macrophages, also the occurrence of multi-nucleated giant cells. All of these are indicative of a greater degree of biocompatibility of the materials of the devices described in this patent application relative to a material in current usage in the fabrication of prosthetic devices.

EXAMPLE 15

Test of thrombogenicity

Healthy adult beagles from an MRC accredited source were used for all thrombogenicity testing.

An in vivo trial was carried out using materials specified in examples 1 and 2. The Material was implanted in two dogs which were allowed to survive for two hours under anaesthesia.

The materials were cut into 4×4 cm sections and conditioned in compound sodium lactate (Hartman's solution B.P.), which approximates to body fluid, for 24 hours prior to insertion. No specific form of cleaning was used to remove particulate matter from the materials, but all containers and instruments used in handling were cleaned sonically.

The animals were anaesthetised with 5% thiopentone sodium i.v. and maintained by oxygen/nitrous oxide by a ventilator. The chest was opened by right thoracotomy and the pericardium opened and sutured out. The side of the atrium was clamped and a section about 20×25 mm was excised. The piece of material was cut to form an ellipsoid patch and was stitched to the atrium with 6/0 Prolene (monofilament polypropylene). The clamp was removed and the normal surgical procedure of holding a swab firmly on the implant was used. It was found that the suture line became leak proof within 5 minutes, the needle holes closing up more rapidly than with standard polyester velour implant material. After two hours the implant and the surrounding tissue was removed.

The experiments showed sufficiently good results to warrant a more extensive trial entailing a 3 week survival. The materials specified in examples 3, 4 and 5 were also included in this group of experiments.

A woven polyester velour (Microvel-Meadow Corporation) was implanted into two dogs as a control. The materials for the survival implants were prepared in the same manner as for the rat trials and full sterile procedures were used at operation. The same protocol was followed as in the 2 hours survival experiments and when the suture line had ceased oozing the chest was closed, an underwater drain being left in the right pleural cavity for 3-4 hours. The dogs were kept sedated until the drain was removed. They were then allowed to recover naturally under constant supervision for the first 24 hours.

There was one death due to surgical technique, but four dogs with each material survived and were healthy, with no complications, for the three weeks.

The initial examination at time of sacrifice showed little thrombus formation in 11 dogs, 1 dog in Material 3 group showed a large amount of thrombus adherent to 85% of the upper surface of the patch. Kidney and liver showed no gross changes in any of the 12 animals.

The two Microvel implants showed injuration at the edgeson both the upper and lower aspects, adherent thrombus, without intimal cover, was observed across the patch. Liver and kidney were normal in appearance. At the site selected the materials tested were superior in terms of low thrombogenicity and biocompatibility to that which is most favoured for current surgical use.

We claim:
1. A biocompatible surgical device comprising a hydrophilic thermoplastic graft copolymer
which is a base polymer, selected from the group consisting of polyolefins, partially or fully fluorinated polyolefins, polyetherurethanes, polydimethyl siloxanes, polyethylene glycol terephthalates, polyamides, polyacrylonitriles, polyvinyl chlorides, polyvinylidene chlorides, polyvinyl pyrolidones and copolymers of the monomers of two or more of said polymers,
graft copolymerized with an ethylenic carboxylic acid by subjecting the base polymer to ionizing radiation in the presence of a monomeric ethylenic carboxylic acid, said surgical device adapted to be implanted into the living mammalian body or applied to the outer surface of the living mammalian body or to function as a body fluid contacting surface in an extra corporeal body fluid treating device.

2. A biocompatible surgical device according to claim 1 wherein the ethylenic carboxylic acid is selected from the group consisting of acrylic acid and alkyl substituted acrylic acids.

3. A biocompatible surgical device according to claim 2 wherein the ethylenic carboxylic acid is methacrylic acid.

4. A biocompatible surgical device according to claim 1 wherein the base polymer is selected from the group consisting of polyethylene, polypropylene, polytetrafluoroethylene, and polyetherurethanes.

5. A biocompatible surgical device according to claim 1 wherein the base polymer is surface graft copolymerised with the ethylenic carboxylic acid.

6. A biocompatible surgical device according to claim 1 wherein the percentage graft copolymerisation of the copolymerised regions is between 5% and 45% by weight.

7. A biocompatible surgical device according to claim 1 wherein the hydrophilic thermoplastic graft copolymer is in the form of a polymetallated salt.

8. A biocompatible surgical device according to claim 7 wherein the salt is a polysodium, polypotassium or a polycalcium salt.

9. A biocompatible surgical device according to claim 1 wherein the graft-copolymerized base polymer is immersed at a temperature in excess of 80° C. in a liquid treatment medium capable of swelling the graft-copolymerized base polymer.

10. A biocompatible surgical device according to claim 9 wherein the liquid treatment medium is glycerol.

11. A biocompatible surgical device according to claim 9 wherein the liquid treatment medium is monoethylene glycol, diethylene glycol, triethylene glycol or polyethylene glycol.

12. A biocompatible surgical device according to claim 1 in the form of a vascular prosthesis.

13. A biocompatible surgical device according to claim 1 in the form of a temporary covering for skin loss or open wounds.

14. A biocompatible surgical device according to claim 1 in the form of a body fluid contacting surface for use in an extra corporeal, body fluid treating device.

15. A biocompatible surgical device according to claim 1 wherein the base polymer is bulk graft copolymerized with the ethylenic carboxylic acid.

* * * * *